US012685837B2

(12) United States Patent
Roeck et al.

(10) Patent No.: US 12,685,837 B2
(45) Date of Patent: Jul. 21, 2026

(54) GAIT STABILIZING WITH HEARING DEVICE

(71) Applicant: SONOVA AG, Staefa (CH)

(72) Inventors: Hans-Ueli Roeck, Hombrechtikon (CH); Niklas Ignasiak, Zürich (CH); Manuela Feilner, Egg b. Zürich (CH)

(73) Assignee: Sonova AG, Staefa (CH)

( * ) Notice: Subject to any disclaimer, the term of this patent is extended or adjusted under 35 U.S.C. 154(b) by 868 days.

(21) Appl. No.: 18/089,822

(22) Filed: Dec. 28, 2022

(65) Prior Publication Data

US 2023/0226309 A1     Jul. 20, 2023

(30) Foreign Application Priority Data

Jan. 18, 2022    (EP) ..................................... 22151898

(51) Int. Cl.
| | |
|---|---|
| *H04R 25/00* | (2006.01) |
| *A61M 21/00* | (2006.01) |
| *H04R 1/10* | (2026.01) |

(52) U.S. Cl.
CPC .............. *A61M 21/00* (2013.01); *H04R 1/10* (2013.01); *A61M 2021/0027* (2013.01); *A61M 2230/62* (2013.01); *A61M 2230/63* (2013.01)

(58) Field of Classification Search
CPC ........... A61B 5/112; A61B 2562/0219; A61B 5/6817; A61B 5/486; A61B 5/746; A61B 5/6803; A61B 5/02438; A61B 5/7282; A61B 5/1116; A61B 5/7405; A61B 5/6815; A61B 5/6801; A61B 5/6802;
(Continued)

(56) References Cited

U.S. PATENT DOCUMENTS

2010/0008524 A1*  1/2010  Burleigh ................ H04R 15/00
                                                                381/190
2018/0289287 A1   10/2018  Sio et al.
(Continued)

FOREIGN PATENT DOCUMENTS

WO      2010039674 A2     4/2010
WO      2010124013 A1     10/2010
(Continued)

OTHER PUBLICATIONS

"Extended European Search Report received in EP Application No. 22151898.8 on Jul. 8, 2022".

*Primary Examiner* — Brian L Casler
(74) *Attorney, Agent, or Firm* — ALG Intellectual Property, LLC

(57) ABSTRACT

A method for stabilizing a gait of a user wearing a hearing device comprises: sensing an audio signal with a microphone of the hearing device; modifying the audio signal with the hearing device into a modified audio signal; sensing a movement signal of the user with a movement sensor of the hearing device; determining a step signal indicative of a timing of steps of the user and/or a sway signal of the user indicative of a sway of the user over time from the movement signal; predicting a future step signal from the step signal; triggering a cue signal depending on the future step signal and/or the future sway signal; generating an output cue to be output to the user, the output cue comprising an acoustic cue; and adding the acoustic cue to the audio signal or the modified audio signal at the timing of the cue signal.

13 Claims, 2 Drawing Sheets

(58) Field of Classification Search
CPC .... A61B 5/6813; A61B 5/4836; A61M 21/00;
A61M 2021/0027; A61M 2230/62; A61M
2230/63; H04R 1/10; H04R 2225/025;
H04R 2225/55; H04R 25/00
USPC ......................................................... 600/27
See application file for complete search history.

(56) References Cited

U.S. PATENT DOCUMENTS

2020/0205746 A1 *    7/2020    Burwinkel ......... G08B 21/0446
2022/0189278 A1 *    6/2022    Hannemann .......... A61B 5/1117

FOREIGN PATENT DOCUMENTS

WO            2016166281 A1    10/2016
WO            2019211016 A1    11/2019
WO        WO-2021050966 A1 *    3/2021    ........... A61B 5/1117

* cited by examiner

GAIT STABILIZING WITH HEARING DEVICE

RELATED APPLICATIONS

The present application claims priority to EP Patent Application No. EP22151898, filed Jan. 18, 2022, the contents of which are hereby incorporated by reference in their entirety.

BACKGROUND INFORMATION

Hearing devices are generally small and complex devices. Hearing devices can include a processor, microphone, speaker, memory, housing, and other electronical and mechanical components. Some example hearing devices are Behind-The-Ear (BTE), Receiver-In-Canal (RIC), In-The-Ear (ITE), Completely-In-Canal (CIC), and Invisible-In-The-Canal (IIC) devices. A user can prefer one of these hearing devices compared to another device based on hearing loss, aesthetic preferences, lifestyle needs, and budget.

Users of hearing devices have a significantly higher risk of also having other comorbidities, e.g. balance problems due to all kinds of causes. A stable, regular gait is considered beneficial to mitigate the risk of falls when walking. Typical problems are e.g. the 'freezing' of the legs among Parkinson patients where a next step is not triggered anymore and thus patients fall over. As well known among physiotherapists, a regular clapping with the hands synchronous to the steps taken by a patient can stabilize his/her gait by providing an additional stimulus to the brain to trigger the next step and stabilize the balance. However, providing a metronome like sound to the user is not a suitable solution though, as it would be considered intrusive and not get accepted.

US 2018 289287 A1 describes a treatment apparatus for treating a gait irregularity of a person. The treatment apparatus comprises a gait irregularity monitoring unit for detecting a gait irregularity of the person, one or more cueing units, such as a loudspeaker, and a cueing control unit for controlling, in response to the detection of the gait irregularity, the one or more cueing units. The adaption of the loudness of the acoustic stimulation to the environmental sound level of the user is described.

WO 2010 124 013 A1 describes a device and method for treating patients with movement disorder associated akinesia. As output device for cues wired or wireless headphones, ear buds or similar devices are proposed. A gait sensor in a headset is proposed.

BRIEF DESCRIPTION OF THE DRAWINGS

Below, embodiments are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION

Figure 1:
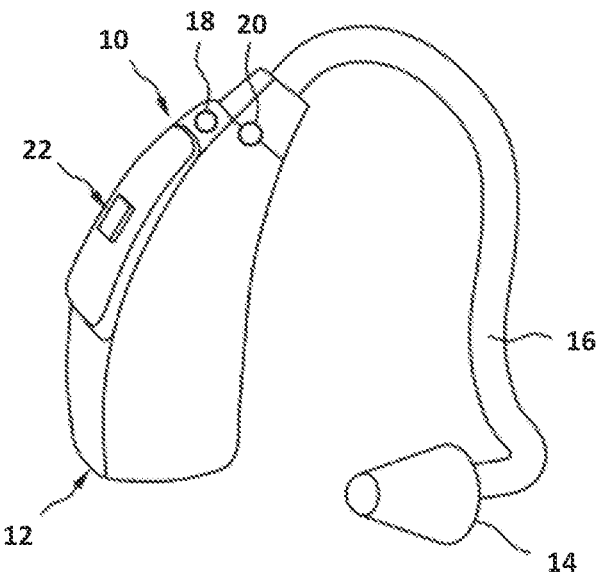
FIG. 1 shows a hearing device according to an embodiment.

Described herein are a method, a computer program and a computer-readable medium for stabilizing a gait of a user of a hearing device. Furthermore, described herein are a hearing system with a hearing device and a mobile device.

It is a feature described herein to provide an automated method, which intends to stabilize the gait and thus potentially prevents falls and to improve the method and devices mentioned above. A further feature is to support hearing devices users, who besides a hearing loss also have Parkinson's disease.

A first aspect relates to a method for stabilizing a gait of a user wearing a hearing device. A hearing device may comprise two components for each ear of the user. The component may comprise parts on the ear, in the ear and/or in the ear channel. The hearing device and/or each of its components may comprise a microphone, a processor and an output device for outputting sound to the user. The method as described herein may be automatically performed by the processor controlling the hearing device.

The method comprises: sensing an audio signal with a microphone of the hearing device. The microphone may sense environmental sounds of the user and may generate an audio signal from it. It has to be understood that the audio signal and also other signals mentioned herein may be a digital signal and/or may be composed of data, i.e. the audio signal may be composed of audio data.

The method further comprises: modifying the audio signal with the hearing device into a modified audio signal, for example to compensate a hearing loss of the user. For example, the audio signal may be frequency dependent amplified and/or attenuated. Also, components of the audio signal may be frequency shifted. This may be done depending on the hearing loss of the user. The operation of the hearing device with respect to modifying the audio signal may be configured by the user and/or an audiologist.

The method further comprises: sensing a movement signal of the user with a movement sensor of the hearing device. The movement sensor may be any further device adapted to sense at least one of the user's steps and sway, such as an acceleration sensor and/or accelerometer. The movement signal may comprise information of the movement of the user and in particular his or her head in three dimensions.

The method further comprises: determining a step signal indicative of a timing of steps of the user and/or a sway signal of the user indicative of a sway of the user over time.

The step signal may be determined by extracting sudden accelerations and/or sudden direction changes from the movement signal. The step signal may comprise information of time points, when a foot of the user touches the ground and/or may differentiate between left and right steps. The step signal may differentiate between step phases (such as toe-off, flying phase, heel strike, foot on the floor).

The sway signal may be determined by removing head movements from the movement signal and/or by extracting left and right movements from the movement signal. The sway signal may comprise information about a left and right movement of the user. The sway signal may differentiate between sway type, such as gait based sway and fall based sway.

It also may be that the step signal is derived and/or predicted from the sway signal and/or that, vice versa, the sway signal is derived and/or predicted from the step signal.

The method further comprises: predicting a future step signal from the step signal, the future step signal indicative of a timing of one or more future steps of the user and/or a future sway signal from the sway signal, the future sway signal indicative of a sway of the user over a future time. The respective signal may be extrapolated into the future for predicting the timing of future steps and/or predicting a future sway. This may be done by extrapolating the respective signal into the future.

The method further comprises: triggering a cue signal depending on the future step signal and/or the future sway signal, such that the cue signal has a timing to cause the user to initiate a next step to stabilize the gait of the user. The cue signal may comprise time points, when an output cue should be output to the user. The cue signal may be synchronized with a periodic step signal and/or periodic sway signal. The pulses of the cue signal may have a constant offset to a phase point of the periodic step signal and/or periodic sway signal, such as a point, where a foot touches the ground, or a sway to a side is maximal.

The method further comprises: generating an output cue to be output to the user, the output cue comprising an acoustic cue. As will be explained below, the output cue also may comprise a cue in the form of an electrical stimulation. The acoustic cue may be an artificial pulsative sound, e.g. claps, noise bursts, click sounds like some shoes, etc. For example, a pulsative sound may be tailored to mimic a natural sound, e.g. a shoe with a hard or soft heel.

A data file storing one or more acoustic cues may be stored in the hearing device. From this data file or otherwise, for example with the aid of a function, a further audio signal may be generated, which contains the acoustic cue.

The method further comprises: adding the acoustic cue to the audio signal or the modified audio signal at the timing of the cue signal. The artificial sounds provided by the acoustic cue may be mixed with the audio signal before the sound processing or to the modified audio signal after the sound processing. As will be described below, a level, frequency and/or type of the acoustic cue may be selected based on environmental conditions and/or features of the step signal and/or sway signal.

The method further comprises: outputting the modified audio signal with the added acoustic cue with a sound output device of the hearing device to the user. Such a sound output device may be a loudspeaker generating sound directed towards a user's tympanic membrane and/or a cochlear implant.

In summary, with the method, at least one of the timing of a probable next future step and a future sway continuation is predicted from the sensor signal of the movement sensor. A timing of a pulsative sound, i.e. the acoustic cue, is based on this and is added to the modified audio signal. Optionally, another actuator, such as an electrode of the hearing device in the ear channel, is triggered with the same timing.

In some instances, by providing the output cue to the user based on the predicted timing of future steps and/or sway, the cue sequence can be adapted, e.g. by taking into account different phases of the stepping and/or swaying movement during a momentary walking step, to an actual walking performance and/or current walking pace, which characteristically is not always steady but can be subject to random and/or chaotic variations and/or external influences. Those step and/or sway variations can thus be taken into account and future states of the step and/or sway can be predicted when outputting the cues to the user for permitting a more natural walking experience, at least to a certain extent, wherein the cue sequence can still be generated within a desired periodicity and/or regularity, e.g. within predefined minimal and/or maximal values of the time intervals between subsequent cues, to also provide for the stabilization of the gait.

In some instances, the providing of the output cue to the user based on the predicted timing of future steps and/or sway can be employed during the onset of a walking activity of the user, e.g. when the user has been in a resting state before the onset of the walking activity. In particular, the predicted timing of future steps and/or sway may be employed to identify an intention of the user to start a walking activity from the resting state and/or initial movement efforts to attain a desired gait performance. E.g., a user suffering from Parkinson's disease can have particular difficulties to perform the first step or steps when having the intention to start the walking activity, and providing the cue sequence in such a situation can be of particular importance to guide the user into performing the subsequent steps.

In some instances, the predicting of the timing of future steps and/or sway can be exploited to identify an occurrence of step and/or sway outliers at an early stage, e.g. for a timely estimation of a fall risk or a freezing of gait, and to allow a provision of countermeasures, e.g. by adjusting a level and/or type and/or head side of the outputted cue sequence, in a timely manner.

In some instances, when the respective timing of the steps and the sway are both taken into account, this can be exploited for an increased accuracy of the overall prediction of the walking behavior, in particular with regard to the prediction of a future step and/or sway. To illustrate, the prediction of a future sway may be carried out not only based on a current and/or previous stepping and/or swaying movement, in particular based on a current or previous phase of the movement during a step taking activity, but also based on the prediction of a future step. Vice versa, the prediction of a future step may be carried out based on the current and/or previous stepping and/or swaying movement and/or based on the prediction of a future sway.

According to an embodiment, the method further comprises: analyzing the step signal and/or the sway signal to determine a fall risk of the user. The fall risk may be a number and/or indicator, how high the risk is that the user will fall during a future time window. This time window may be about the time window, which is needed for one step. The fall risk may rise, when a change in the step signal and/or the sway signal is higher than expected from the future step signal and/or the future sway signal, which was predicted during the previous step. The fall risk may be determined by determining outliers in the step signal and/or sway signal.

According to an embodiment, a level of the output cue and/or a type of the output cue is chosen depending on the fall risk. For example, the output cue only may be output to the user, when the fall risk is higher than a threshold. It also may be that the perceptibility of the acoustic cue is increased depending in the fall risk.

The level of the output cue may be the volume of an acoustic cue and/or the strength of an electric cue. As higher the level, as higher the output cue is perceived by the user.

Different types of output cues may be based on different sound samples (such as claps, noise bursts, click sounds like some shoes, etc.). Different types of output cues also may be based on different shapes of the pulses, of which the output cue is composed.

According to an embodiment, the cue signal is triggered at a time offset with respect to a reference time point and/or reference phase point of the future step signal and/or the future sway signal. The cue signal may be a pulse like signal and/or a series of time instants, which, whenever the output cue should be output to the user, comprises a pulse and/or a time instant. Triggering the cue signal may mean that such a pulse and/or time instant is added to the cue signal.

The step signal and/or the sway signal may be nearly periodic signals with respect to time. A basic period of these signals may be associated with a phase and/or phase angle (such as between 0° and 360°). A specific phase and/or phase angle may be set as reference phase point, such as, for example, 0°, which may be the point, where the sway is maximal to the left and/or the foot touches the ground. The cue signal may be triggered with respect to a specific time offset with respect to this reference phase point and/or reference time point.

It has to be noted that the cue signal is triggered with respect to the future step signal and/or the future sway signal, i.e. a future step and/or a future sway is predicted and the time offset is determined with respect to a reference time point of the future step and/or future sway.

According to an embodiment, a level of the output cue and/or a type of the output cue is chosen depending on a change of the reference time point and/or reference phase point in the future step signal and/or the future sway signal.

In general, the method may take step phases and/or sway types into consideration to issue the trigger of the cue signal at a particular phase and/or time within a step. In view of an irregular step duration, the trigger may be set such that the step duration is stabilized.

According to an embodiment, the future step signal and/or the future sway signal is determined from the step signal and/or the sway signal with at least one of a zeroth order predictor and a first order predictor. A zeroth order predictor may predict the next future step and/or next future sway from the actual step and/or actual sway. A first order predictor may predict the next future step and/or next future sway from the actual and previous step and/or actual and previous sway.

In general, the future step signal and/or the future sway signal may be determined from the step signal and the sway signal by extrapolation. Any suitable statistic method like a mean, a median, etc. applied to the step signal and/or sway signal may be used to predict the future step signal and/or the timing of the next trigger.

According to an embodiment, the method further comprises: determining an environmental sound level from the audio signal. For example, a voice signal of the user's voice may be subtracted from the audio signal. The remaining environmental sound signal may be analyzed in view of the level of the environmental sound.

According to an embodiment, a level of the output cue and/or a type of the output cue is chosen depending on the environmental sound level. For example, the level of the output cue may be chosen, such that the output cue can be distinguished by the user from the environmental sound. The level of the acoustic cue may be adapted such that it is played at a configurable level above/below the environmental sound level to ensure audibility and/or effectiveness of the acoustic cue.

According to an embodiment, a level of the output cue and/or the type of the output cue is adjustable depending on a selectable offset defining a perceptibility of the output cue in the modified audio signal. The offset may be a volume level offset in relation to the current environmental sound level, e.g. so that, depending on the offset, the output cue may be clearly perceptible and/or so that the output cue may be imperceptible but a stimulation of the user takes place due to stochastic resonance. The selectable offset may be selectable by the user via a user interface of the hearing device.

According to an embodiment, the method further comprises: determining a characteristic of the sensed audio signal and/or modified audio signal before the adding of the acoustic cue, wherein the selectable offset is selected depending on the characteristic. The characteristic may be a value and/or indicator. For example, the characteristic may be indicative of a level, a type, a signal-to-noise ratio and/or a spectral property of the respective audio signal. The selectable offset may be dependent on the characteristic and/or type-dependent on the audio signal. In general, a perceptibility threshold may depend on the characteristic and/or type of the audio signal.

According to an embodiment, the method further comprises: determining a type of physical activity and/or the user location from at least one of the audio signal, the movement signal, the step signal and/or the sway signal.

From the audio signal and/or the environmental sound in the audio signal, the environment of the user may be classified. For example, it may be determined, whether the user is indoor or outdoor, whether the user is in a train, etc.

From the movement signal, the step signal and/or the sway signal, it may be determined, whether the user is sedentary, lightly active (e.g. household work), sitting, walking, running cycling, etc., whether he is walking up or down stairs, etc.

According to an embodiment, a level of the output cue and/or a type of the output cue is chosen depending on the type of physical activity and/or the user location. For example, the level of the output cue may be increased, when the user is outdoors. As a further example, the type of acoustic cue may be chosen differently, when the user is walking or running.

According to an embodiment, the level of the output cue and/or the type of the output cue is configurable with respect to the type of physical activity and/or a user location. The user and/or a professional (an audiologist) may configure the context, in which the output cue becomes active. Examples for such contexts are at least one of location, type of physical activity, intensity of the physical activity, etc.

It also may be that the level and/or type of the output cue is configurable by the user. Such a manual setting may be performed with a volume control, enabling and/or selection means provided by the user interface of the hearing device.

According to an embodiment, the method further comprises: choosing a dominant frequency of the acoustic cue depending on a spectral analysis of the audio signal. The audio signal or the environmental sound may be analyzed in view of its frequency spectrum. The sound level adaptation of the acoustic cue may be spectrally shaped according to the environmental sound. The dominant frequency may be in the frequency band with the highest sound level. The acoustic cue may be frequency shifted such that the dominant frequency is at a position, where the audio signal has lower frequency dependent levels. For example, when the user is in a windy environment, the dominant frequency of the acoustic cue may be chosen to be higher than the dominant frequency of the wind noise.

According to an embodiment, the method further comprises: generating an output cue for each ear of the user. The hearing device may comprise two components to be worn at and/or in each ear of the user. Each of these components may be adapted to generate an output cue of its own.

According to an embodiment, the method further comprises: determining a relative level between the output cues for the ears depending on a step side and/or a direction of sway and/or determined from the step signal and/or the sway signal. The acoustical and/or electrical stimulation of the output cue may be tailored such, that depending upon the direction and predicted continuation of sway respectively deviation thereof, the stimulation is predominantly or even exclusively provided on one side of the head. The chosen direction might be dependent upon the type of acoustic cue for acoustic stimulation and/or the type of electrical pulse shape(s), strength and duration of the electric cue.

According to an embodiment, the method further comprises: determining a noise level in at least one of the audio signal and the modified audio signal. The noise level may be a number and/or indictor indicating the level and/or loudness of noise in at least one of the audio signal and the modified audio signal. Such a noise level also may be used for setting the level and/or type of the output cue.

According to an embodiment, the method further comprises: setting a level of the acoustic cue depending on the noise level, such that the acoustic cue is imperceptible by the user but a stimulation of the user takes place due to stochastic resonance. In such a sense, the acoustic cue or more general the output cue may be a perceptible cue or an imperceptible cue. The acoustic cues may be output using effects of stochastic resonances. In this case, the level of sound modification due to the acoustic cue may be below the masking threshold of the environmental sounds.

When the stimulation is based on effects of stochastic resonance, i.e. uses the natural low level noise in the sensory organs (vestibulum, cochlea), this may provide an effective stimulation while being almost or fully imperceptible to the user. The sensory organs have a (noise free) lower detection level threshold, below which an external stimuli is not detectable and thus not perceivable. As no measurement is noise free though, one can utilize such noise to make external stimuli perceivable even in the context of noise. I.e., a stochastic signal such as noise adding up with an external stimuli which by itself is too small to generate a sensory response, generate together in resonance with the peaks of the external stimuli a signal which exceeds neural activation thresholds and thus causes a perceivable event.

According to an embodiment, the output cue comprises an electric cue for stimulating the ear channel of the user at the timing of the cue signal. The electric cue may be output to the user with one or more electrodes of the hearing device. These one or more electrodes may be located in the ear channel. This may be seen as an additional mode of stimulation, which uses an electrical pulse to stimulate the vestibulum.

According to an embodiment, the method further comprises: determining a relative level of stimulation between the acoustic cue and the electric cue depending on a classification of environmental sound in the audio signal; and setting a level of the acoustic cue and the electric cue depending on the relative level. With the relative level, a dominant type of stimulation (either acoustic or electric) may be chosen and/or set. The dominant type of stimulation may be adapted according to at least one of environmental sound. For example, in a noise environment, the level of the electric cue may be increased, while the level of the acoustic cue may be decreased or the acoustic cue even may be switched off.

The relative level of stimulation between the acoustic cue and the electric cue may depend on the type and/or amount of sway as indicated by the sway signal and/or future sway signal. For example, for minimal sway, imperceptive electrical stimulation of low level might be sufficient, whereas for other, stronger sways, acoustical stimulation and/or stronger electrical stimulation might get added.

The relative level of stimulation between the acoustic cue and the electric cue may depend on the type and/or amount of irregularities in the step signal and/or future step signal. Gait rhythm irregularities may be treated predominantly with acoustic stimulation. Vertigo and sway outliers may be treated predominantly with electrical stimulation.

Further aspects relate to a computer program for stabilizing a gait of a user, which, when being executed by a processor of a hearing device, is adapted to carry out the steps of the method as described in the above and in the following as well as to a computer-readable medium, in which such a computer program is stored.

The computer-readable medium may be a memory of this hearing device. In general, a computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code. The computer-readable medium may be a non-transitory or transitory medium.

A further aspect relates to a hearing device, which is adapted for performing the method.

According to an embodiment, the hearing device comprises a microphone for sensing an audio signal; a movement sensor for sensing a movement signal of the user; a sound output device for outputting a modified audio signal to the user; and a processor for performing the method.

In particular, the processor is adapted for: modifying the audio signal with the hearing device into a modified audio signal, for example to compensate a hearing loss of the user; determining a step signal indicative of a timing of steps of the user and/or a sway signal of the user indicative of a sway of the user over time; predicting a future step signal from the step signal indicative of a timing of one or more future steps of the user and/or a future sway signal indicative of a sway of the user over a future time; triggering a cue signal depending on the future step signal and/or the future sway signal, such that the cue signal has a timing to cause the user to initiate a next step to stabilize the gait of the user; generating an output cue to be output to the user, the output cue comprising an acoustic cue; and adding the acoustic cue to the audio signal or the modified audio signal at the timing of the cue signal.

It has to be understood that features of the method as described in the above and in the following may be features of the computer program, the computer-readable medium and the hearing device as described in the above and in the following, and vice versa.

These and other aspects will be apparent from and elucidated with reference to the embodiments described hereinafter.

FIG. 1 schematically shows a hearing device 10, which, as an example, is formed as a behind-the-ear device carried by a user (not shown). It has to be noted that the hearing device 10 is a specific embodiment and that the method described herein also may be performed with other types of hearing devices, such as e.g. an in-the-ear device or one or two of the hearing devices 10 mentioned above.

The hearing device 10 comprises a part 12 behind the ear and a part 14 to be put in the ear channel of the user. The part 12 and the part 14 are connected by a tube 16. The part 12 comprises a microphone 18, a sound output device 20, such as a loudspeaker, and an input mean 22, e.g. a knob, a button, or a touch-sensitive sensor, e.g. capacitive sensor. The microphone 18 can detect a sound in the environment of the user and generate an audio signal indicative of the detected sound. The sound output device 20 can output sound based on the audio signal modified by the hearing device 10, wherein the sound from the sound output device 20 is guided through the tube 16 to the part 14. The input mean 22 enables an input of the user into the hearing device 10, e.g.

in order to power the hearing device 10 on or off, and/or for changing the volume of the hearing device 10 or any other modification of the audio signal.

Figure 2:
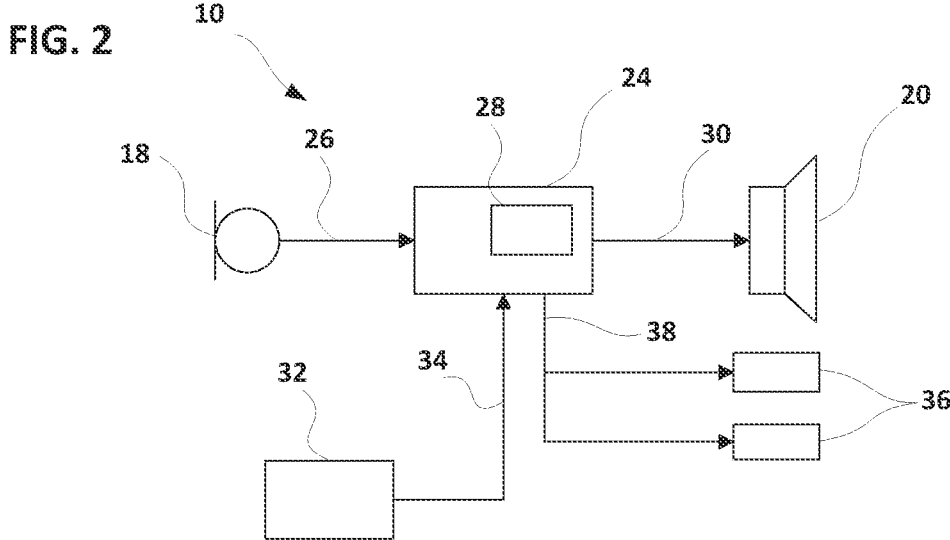
FIG. 2 shows a block diagram of components of a hearing device according to an embodiment.

FIG. 2 shows a block diagram of components of the hearing system 10 according to FIG. 1.

The hearing device 10 comprises a processor 24, which also may comprise peripheral interfaces. The processor 24 is configured to receive the audio signal 26 generated by the microphone 18. The hearing device 10 may include a sound processing module 28. For instance, the sound processing module 28 may be implemented as a computer program executed by the processor 24, which may comprise a CPU for processing the computer program. Alternatively, the sound processing module 28 may comprise a sound processor implemented in hardware or more specific a DSP (digital signal processor) for modifying the audio signal.

The sound processing module 28 may be configured to modify, in particular amplify, dampen and/or delay, the audio signal 26 generated by the microphone 18 to generate a modified audio signal 30. The sound processing module 28 may modify some frequencies or frequency ranges of the audio signal 26 depending on parameter values of parameters stored in the hearing device 10, which influence the amplification, the damping and/or, respectively, the delay. The parameter may be one or more of the group of frequency dependent gain, time constant for attack and release times of compressive gain, time constant for noise canceller, time constant for dereverberation algorithms, reverberation compensation, frequency dependent reverberation compensation, mixing ratio of channels, gain compression, gain shape/amplification scheme.

The sound output device 20 generates sound from the modified audio signal 30 and in the embodiment of FIG. 1, the sound is guided through the tube 16 and the in-the-ear part 14 into the ear channel of the user.

The hearing device 10 also comprises a movement sensor 32, which for example may be an acceleration sensor configured for sensing accelerations, which are caused by the user, when moving his body. The movement sensor 32 generates a movement signal 34, which is received and processed by the processor 24. The movement signal 34 may comprise information on the movement and/or acceleration of the user over time.

FIG. 2 shows that the hearing device 10 optionally comprises electrodes 36, which are configured to apply electric pulses 38 to the user. The electrodes 36 may be provided on a housing of the hearing device 10 and/or on the part 14. The electrodes 36 may be arranged, such that the electric pulses 38 are applied to the ear channel of the user.

Figure 3:
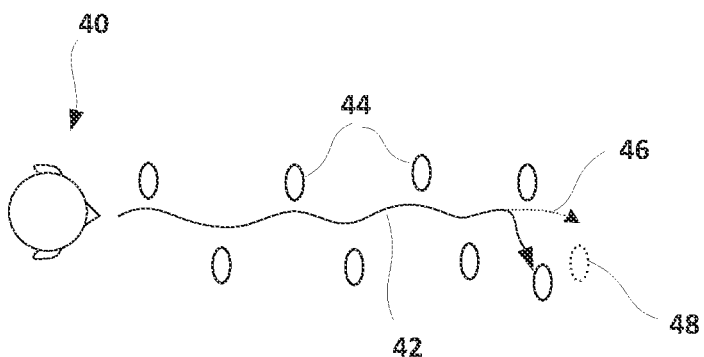
FIG. 3 illustrates a gait of a user of a hearing device according to an embodiment.

FIG. 3 schematically shows the user 40 wearing the hearing device 10 and his or her route, when walking. In FIG. 3, a natural left and right sway while walking and an outlier thereof due to a tripping event is illustrated.

The processor 24 evaluates the movement signal 34 to determine a sway signal 42 and/or a step signal 44, which are indicative of a sway and/or of steps of the user. Based on the sway 42 and/or steps 44, the processor 24 also predicts a future sway signal 46 and/or future step signal 48 by extrapolating the respective signal 42, 44. These signals will be used to generate output cues with the hearing device 10 to stabilize the gait of the user.

Figure 4:
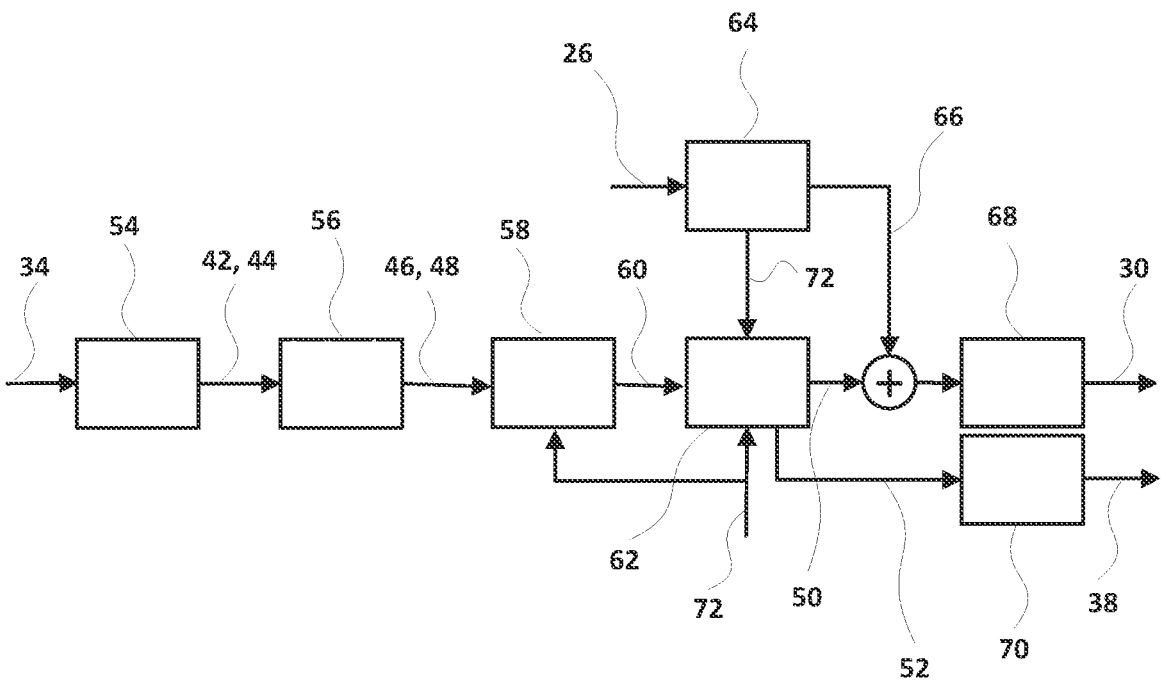
FIG. 4 shows a block diagram illustrating a method according to an embodiment.

FIG. 4 shows a block diagram of parts of the processor 24, which are designed to generate the output cues 50, 52. The part or blocks also may be seen as steps of a method for stabilizing the gait of the user 40 wearing a hearing device 10 that is performed by the processor 24.

FIG. 4 shows that the movement signal 34 of the user 40, which is sensed with the movement sensor 32, is input into a step and sway detector 54. The step and sway detector 54 determines a step signal 44 indicative of a timing of steps of the user 40 and/or a sway signal 42 of the user 40 indicative of a sway of the user 40 over time from the movement signal 34. For example, the timing of steps can be derived by evaluating peaks in an acceleration signal provided by a movement sensor 32 in the form of an acceleration sensor. A sway of the user, in particular in a horizontal direction and orthogonal to a movement direction of the user 40, can be derived by removing head movements, vertical movements and/or constant movements in a specific direction from the movement signal 34.

The sway signal 42 and the step signal 44 are input into a step and/or sway predictor 56, which predicts a future step signal 48 from the step signal 44 indicative of a timing of one or more future steps of the user 40 and/or a future sway signal 46 from the sway signal 42 indicative of a sway of the user 40 over a future time. Such predictions can be made by extrapolating the signals 42, 44 into the future.

The future step signal 48 and/or the future sway signal 46 may be determined from the step signal 44 and/or the sway signal 42 with at least one of a zeroth order predictor and a first order predictor. Features of the step signal 44 and/or the sway signal 42 may be determined, such as time points of step or extrema of the sway signal. These features may be extrapolated into the future, either linear (i.e. with a zeroth order predictor) or also depending on the first derivative of the respective signal (i.e. with a first order predictor).

The future step signal 48 and/or the future sway signal 46 are then input into a cue trigger 58. The cue trigger 58 triggers and/or generates a cue signal 60 depending on the future step signal 48 and/or the future sway signal 46, such that the cue signal 60 has a timing to cause the user 40 to initiate a next step to stabilize the gait of the user 40. The cue signal may be a pulse-like signal and/or may be encoded with a series of time points.

The cue signal 60 is triggered at a time offset with respect to a reference time point of the future step signal 48 and/or the future sway signal 46. Such a reference time point may be a specific feature of the future step signal 48 and/or the future sway signal 46, such as the time point of a next step and/or the time point of an extrema of the future sway signal 46 and/or the future step signal 48. Since these signals 46, 48 usually are repetitive, such a feature may occur repetitive and may be used for identifying a step phase of the user 40. The time offset to the reference time point is chosen to maximize the effect on the user 40 to initiate the next step at the correct time.

The cue signal 60 is input into a cue generator 62, which generates one or more types of output cues 50, 52 to be output to the user 40. The output cues 50, 52 may be acoustic cues 50 and/or electric cues 52.

FIG. 4 further shows that the audio signal 26 is input into an environmental sound processor 64, which preprocesses the audio signal 26 into a preprocessed audio signal 66. For example, wind noise or other environmental signals may be subtracted from the audio signal 26 by the environmental sound processor 64 to generate the preprocessed audio signal 66.

The preprocessed audio signal 66 is then input into a further sound processor 68, which further modifies the preprocessed audio signal 66 into the modified audio signal 30, for example to compensate a hearing loss of the user 40. For example, the preprocessed audio signal 66 may be frequency dependent amplified and/or attenuated. Also, components of the preprocessed audio signal 66 may be frequency shifted.

The environmental sound processor 64 and the further sound processor 68 may be components of the sound processing module 28 as shown in FIG. 2.

In FIG. 4 it is shown that the acoustic cue 50 is added to a preprocessed audio signal 66. However, in general, the acoustic cue 50 also may be added to the audio signal 26 directly. It is also possible that the acoustic cue 50 is added to the modified audio signal 30, after it has been processed by the further sound processor 68. The acoustic cue 50 is added to the audio signal 26, the preprocessed audio signal 66 or the modified audio signal 30 at the timing of the cue signal 60.

It has to be noted that the preprocessing of the audio signal is optional and that the audio signal 26 may be directly input into the further sound processor 68.

It is also possible that the cue generator 62 generates an electric cue 52 for stimulating the ear channel with an electric pulse of the user 40 at the timing of the cue signal 60. The electric cue 52, which (as the acoustic cue 50) may have a specific shape over time as defined by the cue generator 62 is input into an electric pulse generator 70, which transforms the electric cue into an electric pulse 38. The electric cue 52 is then output to the user 40 with the electrodes 36 (see FIG. 2).

The cue generator 62 may be configured and/or designed to choose a level of the output cue 50, 52 and/or a type of the output cue 50, 52 depending on specific characteristics determined in the hearing device 10.

For example, the cue generator 62 analyzes the step signal 44 and/or the sway signal 42 to determine a fall risk of the user 40. This may be done by comparing a previous future step signal 48 and/or future sway signal 46, which has been determined with respect to a time point of a previous step, with the actual step signal 44 and/or the actual sway signal 42. Deviations between these may be indicative of a fall risk. The fall risk may then be used as characteristics to choose the level of the output cue 50, 52 and/or the type of the output cue 50, 52. For example, when the fall risk is high, the acoustic cue may become louder and/or the electric cue may become stronger.

The cue generator 62 also may determine a change of the reference time point in the future step signal 48 and/or the future sway signal 46, which reference time point is used for determining the timing of the cue signal 60. Whenever this timing becomes more irregular, then the acoustic cue may become louder and/or the electric cue may become stronger.

The cue generator 62 also may determine a type of physical activity and/or the user location from at least one of the movement signal 34, the step signal 44 and/or the sway signal 42. For example, the physical activities "sitting", "standing", "walking" and "running" may be discriminated from the signals 42, 44. Locations such as "in car", "in train", "uneven environment" may be determined from the movement signal 42.

As a further example, the environmental sound processor 64 may analyze the audio signal and may determine classifications 72 of the audio signal 26. Such classifications 72 may comprise an environmental sound level, a type of physical activity of the user 40, a location of the user 40, etc. Such classifications also may be used as user characteristics to choose the level of the output cue 50, 52 and/or the type of the output cue 50, 52.

The environmental sound processor 64 may provide a spectral analysis of the audio signal 26 and the cue generator

62. For instance, the environmental sound processor 64 may choose a dominant frequency of the acoustic cue 50 depending on the spectral analysis. In this case, the acoustic cue 50 may be frequency shifted.

The classification 72 of environmental sound also may be used for setting a level of the acoustic cue 50 and the electric cue 52 depending on a relative level, which is determined by the cue generator 62. For example, the environmental sound processor 64 may determine a noise level of the environmental sound and the cue generator 62 may increase the level of the electric cue 52 and decrease the level of the acoustic cue 50 in dependence of the noise level.

A level of the output cue 50, 52 and/or a type of the output cue 50, 52 may be adjustable depending on a selectable offset defining a perceptibility of the output cue 50, 52 in the modified audio signal 30. For example, the selectable offset may be selected with a user interface of the hearing device by the user. As another example, a characteristic of the sensed audio signal 26 and/or modified audio signal 30 may be determined before the adding of the output cue 50. The selectable offset may then be selected depending on the characteristic. As a further example, the selectable offset may be selected depending on the characteristic and/or via the user interface.

To illustrate, a different selection of the offset of the output cue 50, 52 in the modified audio signal 30 can be desirable depending on the characteristic of the sensed audio signal 26, which may be determined by environmental sound processor 64, and/or on the characteristic of the modified audio signal 30, which may be determined by environmental sound processor 64 and/or sound processor 68, e.g., depending on a level, type, signal-to-noise ratio (SNR), spectral property, and/or other characteristic of the respective signal 26, 30. For example, an increased level and/or SNR and/or bandwidth of the environmental sound (corresponding to the sensed audio signal 26) and/or outputted sound (corresponding to the modified audio signal 30) could reduce the perceptibility of the acoustic cue 50. The offset may thus be selected to counteract the reduction of the perceptibility of the output cue 50, 52 to keep the perceptibility at a desired extent, which may be predefined and/or adjusted via the user-interface. A first illustrative example of such an environmental sound and/or outputted sound may be a signal type corresponding to a white noise signal, e.g. at a sound pressure level (SPL) of 60 decibel (dB). The signal type of acoustic cue 50 may be a white noise burst. Selecting the offset at 10 dB would yield the acoustic cue 50 at 70 dB, which could be perceived by the user. Selecting the offset at −10 dB would yield the acoustic cue 50 at 50 dB, which may be imperceivable by the user. A second illustrative example may be a narrowband and/or tonal signal type of the environmental sound and/or outputted sound, e.g. a note of a flute, also having an SPL of 60 dB. When selecting the offset of the white noise burst at −10 dB to provide the acoustic cue at 50 dB, the acoustic cue could still be perceivable by the user. Thus, by adjusting the level of the acoustic cue depending on the level and/or type of the environmental sound and/or outputted sound, the offset can be selected to keep the perceptibility of the acoustic cue at the desired extent. Similarly, by adjusting a type of the acoustic cue, e.g. between a first type which may be a tonal signal and a second type which may be a white noise burst, the offset could be selected accordingly.

As another example, an increased level and/or SNR and/or bandwidth of the environmental sound and/or outputted sound may not only reduce the perceptibility of the acoustic cue 50 but also indicate a decreased attentiveness of the user to the acoustic cue 50, e.g. due to an increased distraction of the user caused by the environmental sound and/or outputted sound. The offset may thus be selected to also counteract the reduced attentiveness of the user, e.g. by increasing the perceptibility of the acoustic cue depending on the level and/or SNR and/or spectral property and/or type of the environmental sound and/or outputted sound. E.g., when determining an environmental sound type indicating a noisy traffic situation, the offset may be selected to provide for a larger perceptibility of the acoustic cue 50, e.g. as compared to the offset selected in a calm household situation, by adjusting the level and/or type of the acoustic cue 50 accordingly. Correspondingly, selecting the offset via the user-interface could also be employed to keep the perceptibility of the output cue 50, 52 at a desired extent, and/or to increase or decrease the perceptibility of the output cue 50, 52 in different situations, e.g. according to a preference of the user.

In the case, when the hearing device 10 has two components, one for each ear of the user 40, also a relative level between the output cues 50, 52 for the ears may be set by the cue generator 62. Note that FIG. 1 then shows one of the components for one ear. The components then may communicate with each other to synchronize the cue generation and/or the cue signals 60.

For example, the relative level between the output cues 50, 52 for the ears may depend on a step side and/or a direction of sway. The step side may be determined from the step signal 44. The sway direction may be determined from the sway signal 42.

As a last example, the level of the acoustic cue 50 may be set by the cue generator 62 based on the phenomena called "stochastic resonance" as described above. The environmental sound processor 64 may determine a noise level in at least one of the audio signal 26 and the modified audio signal 30. The cue generator then may set a level of the acoustic cue 50 depending on the noise level, such that the acoustic cue 50 is imperceptible by the user 40 but a stimulation of the user takes place due to stochastic resonance.

As shown in FIG. 4, parameters of the cue trigger 58 and/or the cue generator 62 are configurable by the user 40 and/or an audiologist, who can input a user configuration 74 into the hearing device 10. For example, the time offset with respect to the reference time point for determining the timing of the cue signal 60 and/or the level and type of the output cues 50, 52 may be changed by changing the user configuration 74.

While the embodiments described herein have been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SYMBOLS

10 hearing device
12 behind the ear part

14 in the ear part
16 tube
18 microphone
20 sound output device
22 input mean
24 processor
26 audio signal
28 sound processing module
30 modified audio signal
32 movement sensor
34 movement signal
36 electrode
38 electric pulse
40 user
42 sway signal
44 step signal
46 future sway signal
48 future step signal
50 output cue, acoustic cue
52 output cue, electric cue
54 step and sway detector
56 step and sway predictor
58 cue trigger
60 cue signal
62 cue generator
64 environmental sound processor
66 preprocessed audio signal
68 further sound processor
70 electric pulse generator
72 classifications

What is claimed is:

1. A method for stabilizing a gait of a user wearing a hearing device, the method comprising:

sensing an audio signal with a microphone of the hearing device;

modifying the audio signal with the hearing device into a modified audio signal;

sensing a movement signal of the user with a movement sensor of the hearing device;

determining at least one of a step signal indicative of a timing of steps of the user or a sway signal of the user indicative of a sway of the user over time from the movement signal;

predicting a future step signal from the step signal, the future step signal indicative of at least one of a timing of one or more future steps of the user or a future sway signal from the sway signal, the future sway signal indicative of a sway of the user over a future time;

triggering a cue signal depending on at least one of the future step signal or the future sway signal, such that the cue signal has a timing to cause the user to initiate a next step to stabilize the gait of the user;

generating an output cue to be output to the user, the output cue comprising an acoustic cue;

adding the acoustic cue to the audio signal or the modified audio signal at the timing of the cue signal;

outputting the modified audio signal with the added acoustic cue with a sound output device of the hearing device to the user, wherein a level of the acoustic cue is set based on a noise level in at least one of the audio signal or the modified audio signal, such that the acoustic cue is imperceptible by the user but a stimulation of the user takes place due to stochastic resonance.

2. The method of claim 1, further comprising:

analyzing at least one of the step signal or the sway signal to determine a fall risk of the user;

wherein at least one of a level of the output cue or a type of the output cue is chosen depending on the fall risk.

3. The method of claim 1, wherein at least one of:

the cue signal is triggered at a time offset with respect to a reference time point of at least one of the future step signal or the future sway signal; or at least one of a level of the output cue or a type of the output cue is chosen depending on at least one of a change of the reference time point in the future step signal or the future sway signal.

4. The method of claim 1, wherein at least one of the future step signal or the future sway signal is determined from the step signal or the sway signal with at least one of a zeroth order predictor and a first order predictor.

5. The method of claim 1, wherein at least one of a level of the output cue or a type of the output cue is adjustable depending on a selectable offset defining a perceptibility of the output cue in the modified audio signal.

6. The method of claim 5, further comprising:

determining at least one of a characteristic of the sensed audio signal or modified audio signal before the adding of the acoustic cue;

wherein the selectable offset is selected depending on the characteristic.

7. The method of claim 1, further comprising:

determining at least one of a type of physical activity or a user location from at least one of the audio signal, the movement signal, the step signal, or and/or the sway signal;

wherein at least one of a level of the output cue or a type of the output cue is chosen depending on at least one of the type of physical activity or the user location.

8. The method of claim 7, wherein at least one of the level of the output cue or the type of the output cue is configurable with respect to at least one of the type of physical activity or a user location.

9. The method of claim 1, further comprising:

choosing a dominant frequency of the acoustic cue depending on a spectral analysis of the audio signal.

10. The method of claim 1, further comprising:

generating an output cue for each ear of the user;

determining a relative level between the output cues for the ears depending on at least one of a step side or a direction of sway.

11. The method of claim 1, wherein the output cue further comprises an electric cue for stimulating an ear channel of the user at the timing of the cue signal;

wherein the electric cue is output to the user with an electrode of the hearing device.

12. The method of claim 11, further comprising:

determining a relative level of stimulation between the acoustic cue and the electric cue depending on a classification of environmental sound in the audio signal;

setting a level of the acoustic cue and the electric cue depending on the relative level.

13. A hearing device, comprising:

a microphone for sensing an audio signal;

a movement sensor for sensing a movement signal of a user;

a sound output device;

a processor for:

modifying the audio signal into a modified audio signal;

determining at least one of a step signal indicative of a timing of steps of the user or a sway signal of the user indicative of a sway of the user over time from the movement signal;

predicting a future step signal from the step signal, the future step signal indicative of at least one of a timing of one or more future steps of the user or a future sway signal from the sway signal, the future sway signal indicative of a sway of the user over a future time;

triggering a cue signal depending on at least one of the future step signal or the future sway signal, such that the cue signal has a timing to cause the user to initiate a next step to stabilize a gait of the user;

generating an output cue to be output to the user, the output cue comprising an acoustic cue;

adding the acoustic cue to the audio signal or the modified audio signal at the timing of the cue signal;

outputting the modified audio signal with the added acoustic cue with the sound output device to the user, wherein a level of the acoustic cue is set based on a noise level in at least one of the audio signal or the modified audio signal, such that the acoustic cue is imperceptible by the user but a stimulation of the user takes place due to stochastic resonance.

*   *   *   *   *